(12) United States Patent
Esser et al.

(10) Patent No.: US 8,058,060 B2
(45) Date of Patent: Nov. 15, 2011

(54) CULTURE INSERT CARRIER, CULTURE INSERT AND CULTURE INSERT SYSTEM

(75) Inventors: Peter Esser, Copenhagen (DK); Frank T. Stigborg, Rodovre (DK); Klaus Pedersen, Copenhagen (DK); Stefan Iskov, Roskilde (DK)

(73) Assignee: Nunc A/S, Roskilde (DK)

( * ) Notice: Subject to any disclaimer, the term of this patent is extended or adjusted under 35 U.S.C. 154(b) by 787 days.

(21) Appl. No.: 11/916,677

(22) PCT Filed: Jun. 9, 2006

(86) PCT No.: PCT/DK2006/000325
§ 371 (c)(1),
(2), (4) Date: Apr. 2, 2008

(87) PCT Pub. No.: WO2006/131123
PCT Pub. Date: Dec. 14, 2006

(65) Prior Publication Data
US 2008/0194017 A1      Aug. 14, 2008

(30) Foreign Application Priority Data
Jun. 10, 2005   (DK) ................................ 2005 00857

(51) Int. Cl.
*C12M 1/22* (2006.01)
(52) U.S. Cl. ............... 435/305.2; 435/287.8; 435/297.5; 435/304.2; 435/305.1; 435/305.3; 435/305.4; 422/551; 422/552; 422/553
(58) Field of Classification Search ............... 435/287.8, 435/297.5, 304.2, 305.1–305.4; 422/551–553
See application file for complete search history.

(56) References Cited

U.S. PATENT DOCUMENTS 4,871,674 A * 10/1989 Matsui et al. .............. 435/297.5
5,026,649 A *  6/1991 Lyman et al. .............. 435/297.5
(Continued)

FOREIGN PATENT DOCUMENTS
EP          0764718          3/1997
(Continued)

OTHER PUBLICATIONS

Japanese Office Action dated Apr. 26, 2011 for related Japanese Patent Application No. 2008-515048.

*Primary Examiner* — Michael Marcheschi
*Assistant Examiner* — Jameson Ma
(74) *Attorney, Agent, or Firm* — Volentine & Whitt, PLLC

(57) ABSTRACT

The present invention relates to a culture insert carrier, a culture insert and a culture system for culturing and testing of different kinds of cells, such as for example skin models. A culture insert carrier for supporting at least one culture insert in a culture tray having at least one well, wherein the culture insert carrier comprises a plane member with at least one opening for insertion of the at least one culture insert in such a way that the culture insert carrier supports the at least one culture insert in a position in the culture tray is provided. Further, a culture insert comprising a plurality of suspension elements including a first set of suspension elements and a second set of suspension elements, the suspension elements being adapted to suspend the culture insert in a plurality of vertical positions, including a first vertical position and a second vertical position, in relation to a frame is provided.

5 Claims, 14 Drawing Sheets

U.S. PATENT DOCUMENTS

| | | | |
|---|---|---|---|
| 5,215,920 A * | 6/1993 | Lyman et al. | 435/297.5 |
| 5,358,871 A | 10/1994 | Stevens et al. | |
| 5,466,602 A * | 11/1995 | Lyman et al. | 435/297.1 |
| 5,468,638 A * | 11/1995 | Barker et al. | 435/304.1 |
| 5,534,227 A | 7/1996 | Lahm et al. | |
| 5,578,492 A * | 11/1996 | Fedun | 435/297.5 |
| 5,652,142 A * | 7/1997 | Barker et al. | 435/297.1 |
| 5,710,043 A * | 1/1998 | Pay | 435/297.5 |
| 5,795,775 A | 8/1998 | Lahm et al. | |
| 5,801,055 A * | 9/1998 | Henderson | 435/297.5 |
| 5,948,363 A * | 9/1999 | Gaillard | 422/552 |
| 6,037,141 A * | 3/2000 | Banes | 435/30 |
| 7,598,076 B2 * | 10/2009 | Wedell et al. | 435/297.5 |
| 2003/0215940 A1 | 11/2003 | Lacey | |
| 2008/0076170 A1 * | 3/2008 | Annala et al. | 435/297.4 |

FOREIGN PATENT DOCUMENTS

JP          2004521644          7/2004

* cited by examiner

CULTURE INSERT CARRIER, CULTURE INSERT AND CULTURE INSERT SYSTEM

CROSS REFERENCE TO RELATED APPLICATIONS

This application is the national phase under 35 U.S.C. 371 of PCT International Application No. PCT/DK2006/000325 which has an international filing date of Jun. 9, 2006, and also claims priority under 35 U.S.C. 119 to Danish application PA 2005 00857 filed on Jun. 10, 2005, which applications are hereby incorporated by reference in their entirety for all purposes as if fully set forth herein.

The present invention relates to a culture insert carrier, a culture insert and a culture system for culturing and testing of different kinds of cells, such as for example skin models.

BACKGROUND OF THE INVENTION

In recent years there has been a growing activity within the field of culturing cells on polymer membranes in culture inserts, such as for example when producing skin models for testing the effect of chemicals, in e.g. cosmetics or skin care products, and/or pharmaceutical products on cells. Use of such skin models reduces the need for experiments on animals.

European patent application EP 0 764 718 discloses an in vitro culture assembly with a culture vessel and a culture insert. The culture vessel has at least one well having a sidewall with a plurality of steps projecting inwardly from the inner surface of the well.

SUMMARY OF THE INVENTION

Thus there is a need for a device to provide a more effective manual and automatic handling of culture inserts.

According to a first aspect of the present invention, a culture insert carrier for supporting at least one culture insert in a culture tray having at least one well is provided. The culture insert carrier comprises a plane member with at least one opening for insertion of the at least one culture insert in such a way that the culture insert carrier supports the at least one culture insert in a position in the culture tray.

The culture insert carrier may support at least one culture insert such that the at least one culture insert has a well-defined lateral position in the culture tray.

The culture insert carrier may be adapted to support at least one culture insert in a plurality of vertical positions, such as a first vertical position and a second vertical position. Further, the culture insert carrier may be adapted to support at least one culture insert in a third vertical position.

The different features of the invention are described in relation to a conventional rectangular system of coordinates having three axes X, Y and Z with mutual angles of 90°. The XY-plane is the plane defined by the axes X and Y, the XZ-plane is the plane defined by the axes X and Z, and the YZ-plane is the plane defined by the axes Y and Z.

During intended operational position of the culture insert in the culture insert carrier, the Z-axis extends in a vertical direction, and the plane member extends in the XY-plane.

A vertical position is defined as a position along the Z-axis.

A lateral position is a position in a plane parallel to the XY-plane.

The at least one opening may comprise a first support element with a bottom and a top and being shaped to support a culture insert. The first support element may extend substantially perpendicular to the plane member.

Preferably, the top of a support element is aligned with the plane member. The bottom of a support element may extend below the plane member in such a way that the support element is submerged into a culture well of a culture tray when the culture insert carrier is engaged with the culture tray.

The plane member comprises at least one opening. The at least one opening may comprise a plurality of openings, such as for example 2, 6, 12, 24, 48 or 98 openings for insertion of culture inserts. Preferably, the respective openings in a culture insert carrier have the same shape and size, however different size and/or shape of the respective openings may be employed, e.g. to accommodate different culture inserts.

Preferably, the one or more openings are shaped, such that when a culture insert is inserted in the one or more openings, an area of the opening remains non-obstructed for enabling e.g. pipette access to a well of a culture tray through the opening when the culture insert carrier accommodating a culture insert is placed on the culture tray.

The one or more openings may comprise a plurality of notches that are formed for reception and accommodation of one or more suspension elements, such as protrusions, of a culture insert. Such notches may in cooperation with the one or more suspension elements of a culture insert prevent the culture insert from rotating. A culture insert may be supported on an edge of the culture insert carrier, e.g. a culture insert may rest on a part of the edge of an opening.

Preferably, the insert carrier according to the invention is adapted for use in cooperation with culture trays according to the SBS-standard.

The first support element may comprise a first rim extending substantially parallel to the plane member for supporting a culture insert. Further, the first support element may comprise a first set of rims. The first set of rims may be positioned in a plane substantially parallel to the plane member. Alternatively the first set of rims may be positioned in the same and/or different planes substantially parallel to the plane member. Preferably the first rim and/or the first set of rims are positioned near the bottom of the first support element.

The first support element may comprise at least one recess. The at least one recess may be adapted to guide a culture insert during insertion in the carrier. The first support element may comprise a first recess or a first set of recesses. The first recess or the first set of recesses may form the first rim or the first set of rims.

Further, the at least one opening may comprise a second support element with a bottom and a top and being shaped to support the culture insert. The second support element may extend substantially perpendicular to the plane member.

The second support element may comprise a second rim extending substantially parallel to the plane member for supporting a culture insert. Further, the second support element may comprise a second set of rims. The second set of rims may be positioned in a plane substantially parallel to the plane member. Alternatively the second set of rims may be positioned in the same and/or different planes substantially parallel to the plane member. Preferably the second rim and/or the second set of rims are positioned near the bottom of the second support element.

The second support element may comprise at least one recess. The at least one recess may be adapted to guide a culture insert during insertion in the carrier. The second support element may comprise a second recess or a second set of recesses. The second recess or the second set of recesses may form the second rim or the second set of rims.

Further, the at least one opening may comprise a third support element with a bottom and a top and being shaped to support the culture insert. The third support element may extend substantially perpendicular to the plane member The third support element may comprise a third rim extending substantially parallel to the plane member for supporting a culture insert. Further, the third support element may comprise a third set of rims. The third set of rims may be positioned in a plane substantially parallel to the plane member. Alternatively the third set of rims may be positioned in the same and/or different planes substantially parallel to the plane member. Preferably the third rim and/or the third set of rims are positioned near the bottom of the third support element.

The third support element may comprise at least one recess. The at least one recess may be adapted to guide a culture insert during insertion in the carrier. The third support element may comprise a third recess or a third set of recesses. The third recess or the third set of recesses may form the third rim or the third set of rims.

Preferably, the first, second and third rim are positioned in the same plane substantially parallel to the plane member of the culture insert carrier.

Preferably, the one or more recesses in the support elements provide a guide to a culture insert during insertion in the culture insert carrier. Further, the recesses may ensure that the culture inserts are substantially rotationally fixed along an axis substantially perpendicular to the plane member when culture inserts are positioned in the carrier.

Preferably, the width and/or the depth of the one or more recesses increase from the bottom towards the top of a support element, such that an easier insertion of a culture insert into the carrier is provided. Guiding of a culture insert during insertion into a carrier further enhances the user-friendliness of the system.

Preferably, the first, second and third support elements have substantially the same shape, e.g. the first, second and third rims may extend in the same plane parallel to the plane member and the first, second and third recesses may have substantially the same dimensions.

It is to be understood that an opening may comprise more than three, such as four, five, six, seven, eight, nine, or more, support elements. Support elements may form sets of support elements, each set being adapted for supporting a culture insert in a vertical position.

In one embodiment, one or more of the support elements, such as the first support element, second support element and/or the third support element, may comprise one or more protrusions to engage with a corresponding suspension element of a culture insert, such as one or more recesses formed in an outer surface of a culture insert, for supporting the culture insert having one or more recesses on the outer surface in at least one vertical position, such as a first, a second and/or a third vertical position. Support element(s) having one or more protrusions for engagement with corresponding recess(es) in a culture insert may be combined with support element(s) having one or more recesses for engagement with corresponding protrusion(s) in a culture insert.

Preferably, the culture insert carrier according to the invention is made of a polymer, such as for example polystyrene, polypropylene, polyethylene, ABS, PMMA, polycarbonate or other suitable materials.

It is an important advantage of the invention that the position of a culture insert in a well of a culture tray is well defined in a plane parallel to the plane member of the culture insert carrier when the culture insert is positioned in a vertical position in the culture insert carrier, thus providing easier manual and automatic handling of culture inserts.

Furthermore, it is an important advantage of the invention that culture inserts in a culture insert carrier can be handled, e.g. moved from one tray to another, both individually and together.

Further, positioning of a culture insert in a plurality of vertical positions in a carrier and in a culture tray is an advantage when adjusting the level or amount of culture medium in respective well or wells of the culture tray.

The invention provides a faster manual and automatic handling of culture inserts. All culture inserts positioned in a culture tray can be moved from one culture tray to another in one operation by moving the culture insert carrier with the culture inserts instead of moving one culture insert at a time.

The culture insert carrier may further comprise at least one support member for supporting the culture insert carrier when the culture insert carrier is placed on a flat surface. Preferably, the support member comprises a plurality of legs, such as for example two three or four legs that may be tube-shaped.

In addition to the one or more openings, the culture insert carrier may further comprise one or more pipette openings to provide pipette access in a corner or at an edge of a well of a culture tray.

According to a further aspect of the invention, a culture insert with a culture insert body and a plurality of suspension elements is provided. Preferably, the culture insert body comprises at least one sidewall with an inner surface and an outer surface and extending from a first end to a second end of the culture insert body, a porous membrane positioned at the first end, a chamber delimited by the porous membrane and the at least one sidewall and having an opening at the second end. The suspension elements are adapted to suspend the culture insert in a plurality of vertical positions, including a first vertical position and a second vertical position, in relation to a frame.

According to the invention, a culture insert with a tubular sidewall comprising an inner surface and an outer surface and extending from a first end to a second end of the sidewall, a porous membrane positioned at the first end, a chamber delimited by the porous membrane and the sidewall and having an opening at the second end, and a plurality of suspension elements is provided. The suspension elements are adapted to suspend the culture insert in a plurality of vertical positions in relation to a frame.

Preferably, a culture insert carrier constitutes the frame, but a tray having at least one well may also function as the frame.

Preferably, the membrane extends in a plane parallel to the XY-plane. Preferably, the at least one sidewall extends from a first end to a second end along an axis, which is parallel to the Z-axis.

Preferably, the first end of the at least one sidewall lies in a plane parallel to the XY-plane. Preferably, the second end of the sidewall lies in a plane parallel to the XY-plane. The at least one sidewall may have one or more cutouts, e.g. from the second end towards the first end.

The suspension elements of the culture insert according to the invention may interact with one or more support elements in a frame in such a way that the culture insert can be positioned in at least a first and a second vertical position when the culture insert is positioned in the frame. In a preferred embodiment the culture insert may also be positioned in a third vertical position.

The culture insert may be substantially rotationally fixed in the first, second and/or third vertical position. This means that the culture insert may be substantially prevented from rotating around an axis parallel to the Z-axis.

A rotationally fixed culture insert provides a well-defined position of the culture insert around an axis parallel to the Z-axis. This is an advantage when handling the inserts manually or automatically, e.g. with tools for moving a culture insert.

The suspension elements may comprise one or more projecting parts, such as one or more protrusions. The one or more projecting parts may comprise one or more flanges extending from the second end and/or the outer surface of the sidewall. In one embodiment of the present invention, the suspension elements comprise one or more recesses or sets of recesses in the outer surface of the culture insert. Preferably, the one or more recesses extend from the first end towards the second end. One or more projecting parts and/or one or more recesses may be combined to form the suspension elements. A suspension element of the culture insert may be formed as a recess in the outer surface or as a protrusion extending from the outer surface of the culture insert body.

The plurality of suspension elements may comprise one or more sets of suspension elements, such as a first set of suspension elements, a second set of suspension elements and/or a third set of suspension elements. A set of suspension elements may comprise a plurality of suspension elements, such as two, three, four, five, six or more suspension elements. One or more protrusions and/or one or more recesses may form a set of suspension elements.

The suspension elements may comprise at least one set of protrusions. Preferably, the suspension elements comprise a first set of protrusions or recesses. More preferably, the suspension elements comprise a second set of protrusions or recesses. Further, the suspension elements may comprise a third set of protrusions or recesses. Preferably, the culture insert according to the invention is in the first, second and third vertical position of the culture insert suspended by means of the first, second and third set of protrusions or recesses, respectively. The culture insert may in the second and/or third vertical position be suspended by means of the first set of protrusions or recesses. A fourth set of protrusions or recesses may be employed.

The first, second and third set of protrusions or recesses for suspension of the culture insert may comprise two, three, four or more protrusions or recesses, respectively. The protrusions or recesses of a set of protrusions or recesses may extend in the Z-direction along the outer surface of the culture insert. Preferably, the protrusions are flush with the second end of the sidewall of the culture insert.

Preferably, a set of protrusions or recesses, e.g. the first, second and third set of protrusions or recesses respectively, comprises three protrusions or recesses to provide a stable suspension of the culture insert.

Preferably, the protrusions or recesses of a set extend from positions on the outer surface, residing in substantially the same plane parallel to the XY-plane. However in another embodiment, protrusions or recesses within a set may extend from different vertical positions on the outer surface.

The first, second and third sets of protrusions or recesses may extend from first, second and third vertical positions on the outer surface in first, second and third planes respectively, the planes being substantially parallel to the XY-plane. Preferably, each protrusion extends towards the second end such that each protrusion forms a ridge or bead extending substantially along the Z-axis on the outer surface. Preferably, the first vertical position on the outer surface is closer to the second end than the second and/or third vertical position on the outer surface. Preferably, the second vertical position on the outer surface is closer to the second end than the third vertical position on the outer surface Preferably, the protrusions or recesses of a set of protrusions or recesses are substantially evenly distributed around the outer surface in a plane substantially parallel to XY-plane. For example a mutual angular distance of about 180° is preferred when a set of protrusions or recesses consists of two protrusions or recesses, a mutual angular distance of about 120° is preferred when a set of protrusions or recesses consists of three protrusions or recesses, and a mutual angular distance of about 90° is preferred when a set of protrusions or recesses consists of four protrusions or recesses.

Preferably, the protrusions or recesses are substantially evenly distributed around the outer surface in a plane substantially parallel to the XY-plane. For example, when having three sets of protrusions or recesses each set consisting of three protrusions or recesses, the mutual angular distance in a plane parallel to the XY-plane between the nine protrusions or recesses in total may be about 40°. Thus, the mutual angular distance in a plane parallel to the XY-plane between a protrusion or recess of one set of protrusions or recesses and the nearest protrusion or recess of a different set of protrusions or recesses is in this case equal to about 40°. Having two sets of protrusions or recesses each consisting of three protrusions or recesses results in a mutual angular distance in a plane parallel to the XY-plane between the six protrusions or recesses in total of about 60°.

The first end of the at least one sidewall may have a flange extending from the inner surface to provide an edge for fixing the membrane.

The culture insert may be provided with a plurality of supports or feet, e.g. two, three, four or more feet, for maintaining a minimum distance between the membrane and a surface, e.g. between the membrane and the bottom of a well of a culture tray.

The culture insert body may have any suitable shape. In a preferred embodiment of the present invention, the culture insert body comprises a tubular sidewall.

The culture insert body may taper from one end towards the other end, such as from the second end towards the first end, and the culture insert body may comprise a plurality of sidewalls, such as two, three, four, five, or more sidewalls.

A culture insert having protrusions as suspension elements may be advantageous when using the culture insert in a well of a culture tray without suspending the culture insert. The protrusions of the culture insert may ensure that the sidewall of the culture insert is kept at a distance from the sidewall of the well thereby minimizing unwanted capillary action of the fluid in the well.

Preferably, the culture insert except from the membrane is made of a polymer, such as for example polystyrene, polypropylene, polyethylene, ABS, PMMA, polycarbonate or other suitable materials, and the membrane may be a polymer membrane such as polycarbonate.

According to a further aspect of the invention, a culture system comprising a culture insert carrier according to the description and a culture insert comprising a membrane and at least one suspension element is provided. The culture insert may comprise a first set of suspension elements and/or a second set of suspension elements.

The culture system may further comprise a culture tray having at least one well.

Preferably, the bottom of the at least one wells of the culture tray extends in a plane parallel to the XY-plane.

Furthermore, a culture system comprising a culture insert carrier according to the description and a tray having at least one well is provided. The culture system may further comprise a culture insert having a membrane and at least one suspension element.

The culture tray may have at least one well. A culture tray having one, two, six, twelve or more wells may be employed.

If a culture tray having one well is employed, all culture inserts positioned in the culture insert carrier share the same well and thus the same culture medium. The pipette openings in the culture insert carrier may in this situation facilitate complete emptying of the culture tray, e.g. for adding a new culture medium to the well. A culture tray having the same number of wells as the number of openings for culture inserts in the culture insert carrier may also be employed such that each well in the culture tray only accommodates one culture insert.

The system may further comprise a lid. The lid may be a standard lid for a culture tray complying with the SBS-standard, such as Nunc's lid for a multidish.

DETAILED DESCRIPTION OF THE INVENTION

Figure 1:
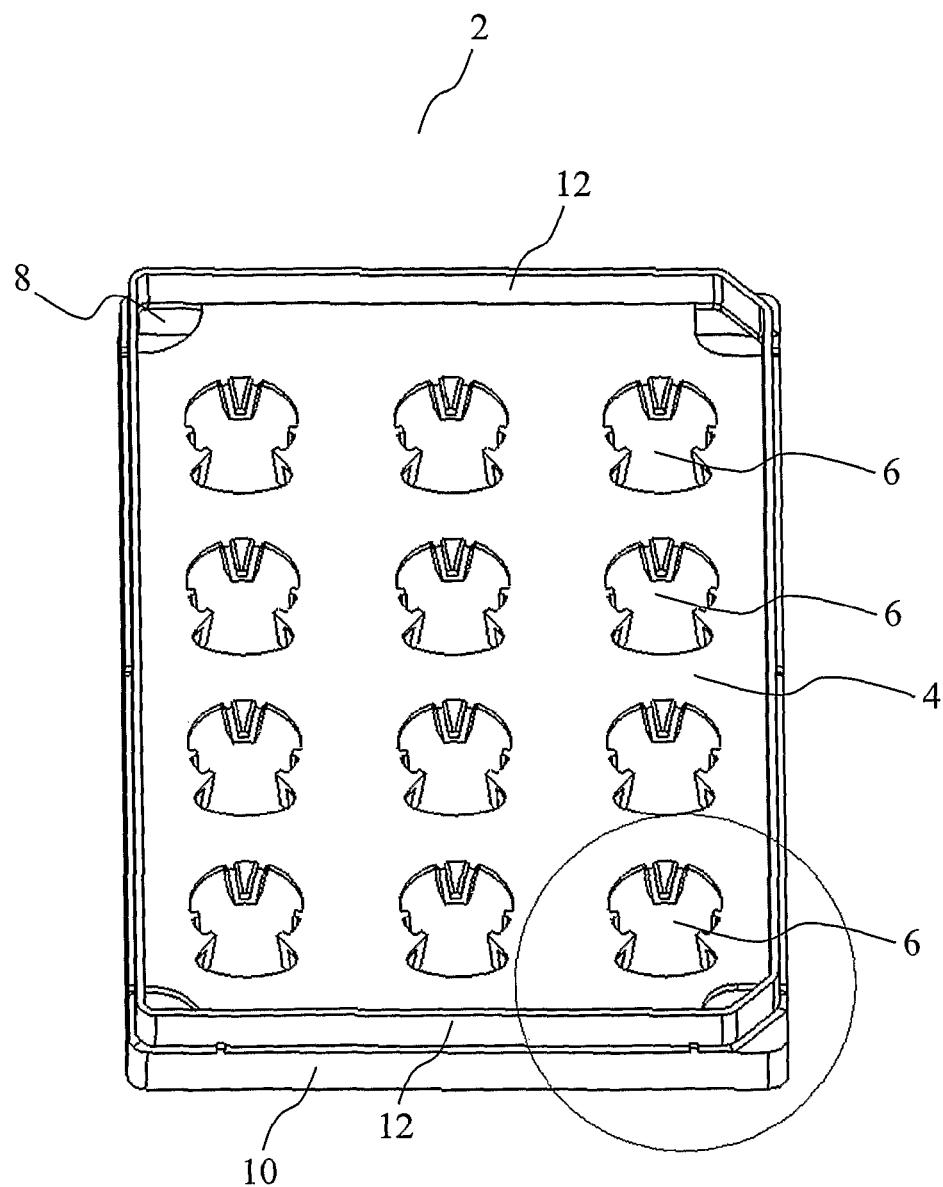
FIGS. 1-5 show a preferred embodiment of the culture insert carrier according to the invention from different perspectives.

FIG. 1 is a perspective view of one embodiment of the culture insert carrier 2 according to the invention. The culture insert carrier has a plane member 4 with twelve openings 6. The plane member further comprises four pipette openings 8 in each corner of the plane member. The culture insert carrier further comprises four sidewalls 10 to provide easy engagement with a culture tray having at least one well. The culture insert carrier 2 further has four sidewalls 12 extending perpendicular to the plane member along the edge of the plane member to provide easy engagement with a lid. The culture insert carrier 2 is adapted for use in cooperation with culture trays according to the SBS-standard.

Figure 2:
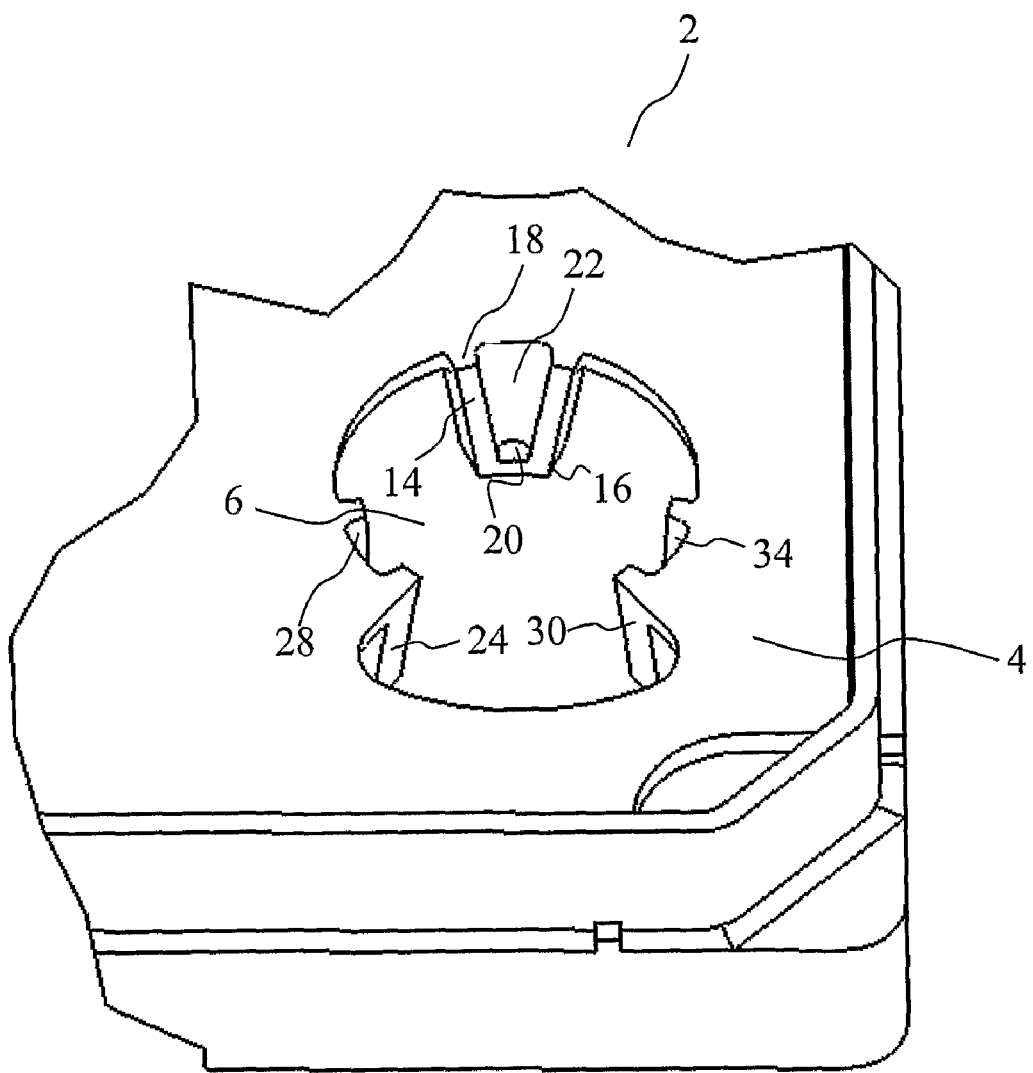

FIG. 2 is an enlarged view of a part of the culture insert carrier 2. The opening 6 has a first support element 14 with a bottom 16 and a top 18. The bottom 16 extends below the plane member 4. The first support element 14 has a first rim 20 extending substantially parallel to the plane member 4 near the bottom of the first support element. The first support element 14 has a first recess 22 that is adapted to guide a culture insert during insertion in the culture insert carrier. The first recess 22 forms the first rim 20. The width of the first recess 22 increases from the bottom 16 towards the top 18 of the first support element, such that an easier insertion of a culture insert is provided.

The opening 6 further comprises a second support element 24 having a second rim 26 formed by a second recess 28, and a third support element 30 having a third rim 32 formed by a third recess 34.

In this embodiment, the first, second and third support elements have substantially the same shape, e.g. the first, second and third rims extend in the same plane parallel to the plane member and the first, second and third recesses have substantially the same dimensions.

The first, second and third recesses 22, 28, 34 guide a culture insert during insertion in the culture insert carrier and prevent the culture insert from rotating around an axis parallel to the Z-axis during and after insertion of the culture insert in the culture insert carrier.

Figure 3:
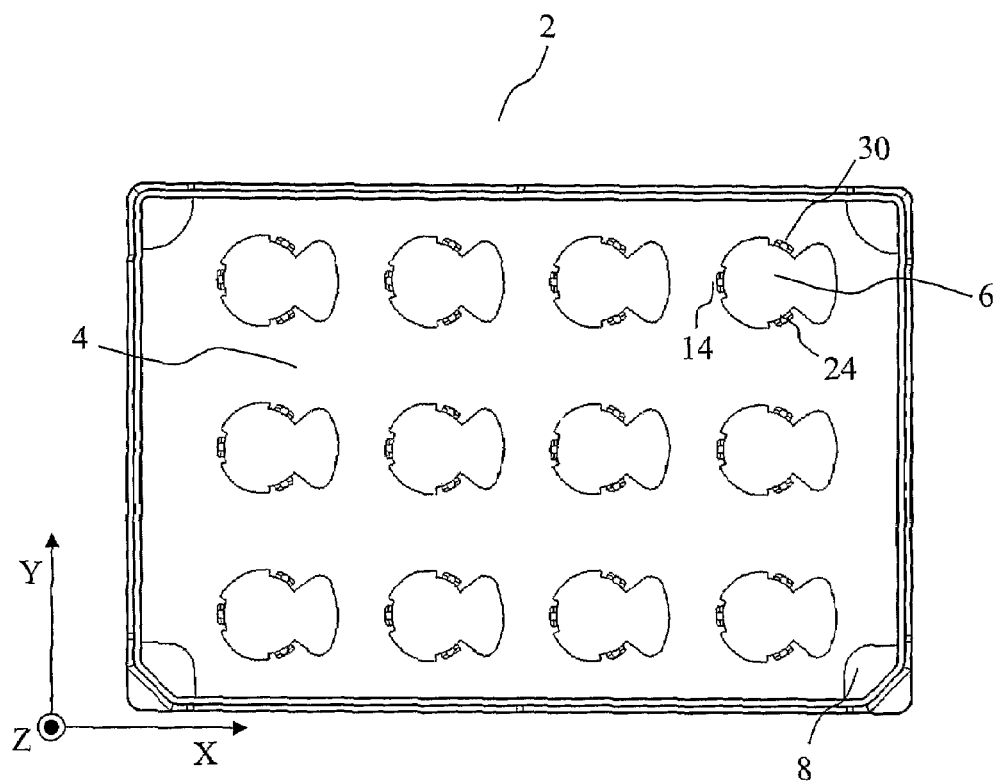

FIG. 3 shows the culture insert carrier 2 from above. The plane member 4 extends in the XY-plane.

Figure 4:
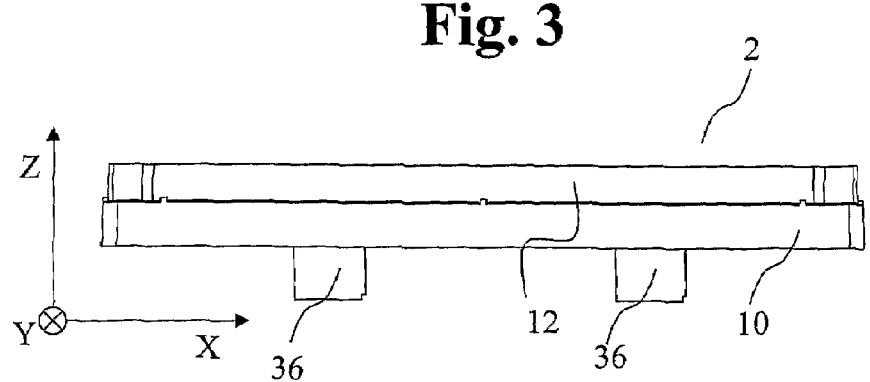

FIG. 4 shows the culture insert carrier 2 seen from the side. The culture insert carrier has four tube-shaped legs 36 of which two can be seen on the figure.

Figure 5:
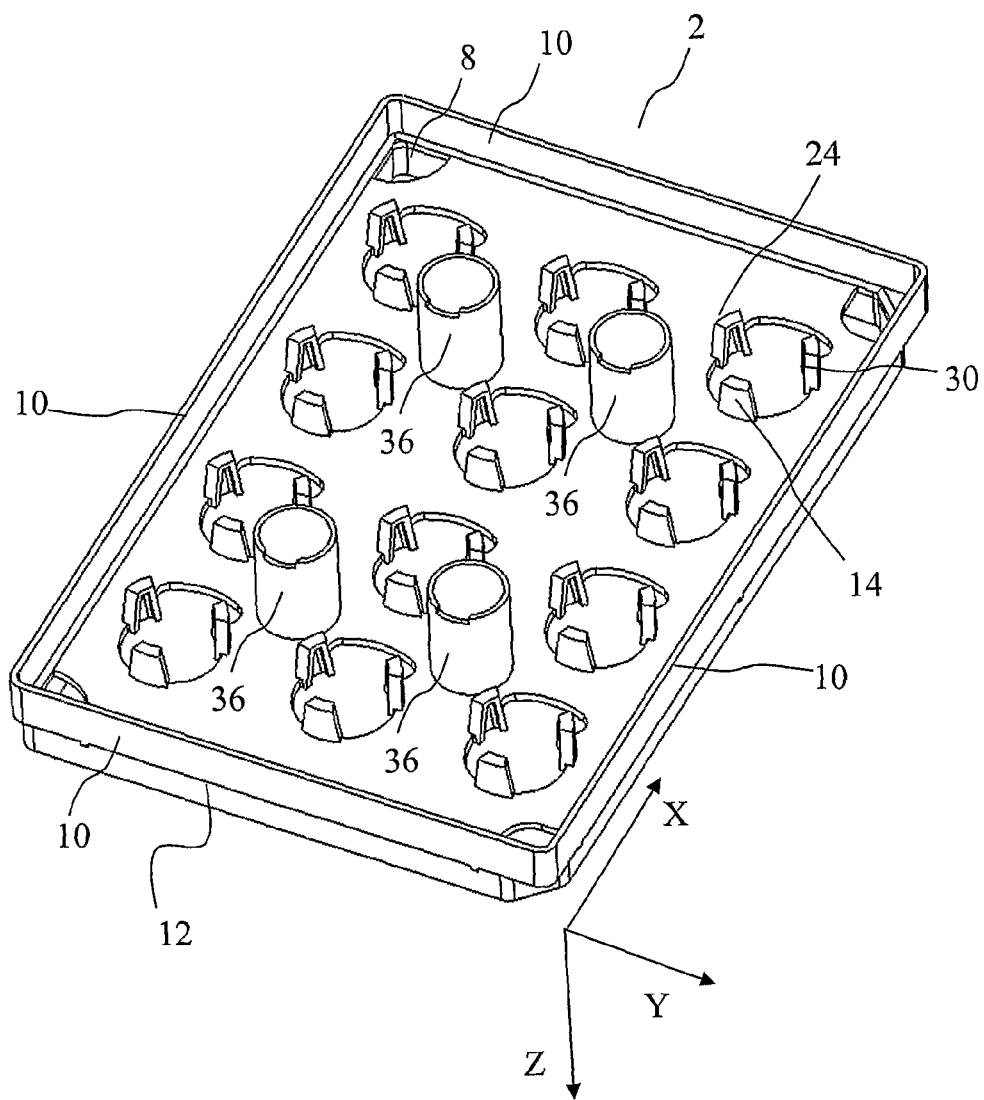

FIG. 5 shows a perspective view of the underside of the culture insert carrier 2. The culture insert carrier has four tube shaped legs 36 to enable positioning of the culture insert carrier with culture inserts on a flat surface substantially without the inserts being moved from their position in the culture insert carrier.

Figure 6:
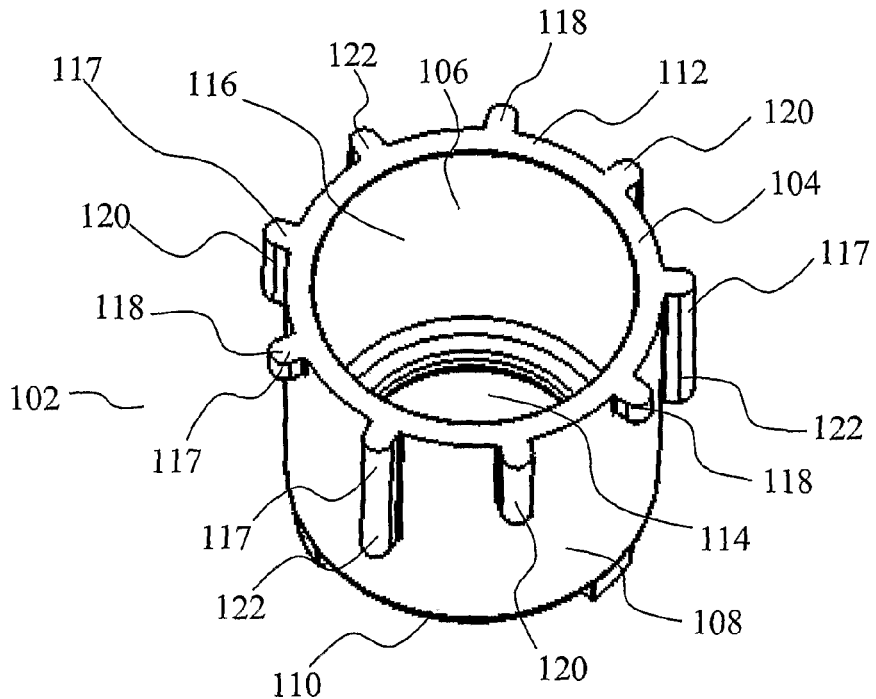
FIGS. 6-9 show a preferred embodiment of the culture insert according to the invention from different perspectives.

FIG. 6 shows a perspective view of one embodiment of a culture insert according to the invention. The culture insert 102 has a tubular sidewall 104 comprising an inner surface 106 and an outer surface 108 and extending from a first end 110 to a second end 112 of the sidewall, a porous membrane 114 positioned at the first end, a chamber delimited by the porous membrane and the sidewall and having an opening 116 at the second end, and a plurality of suspension elements 117, wherein the suspension elements are adapted to suspend the culture insert in a plurality of vertical positions in relation to a frame.

Figure 7:
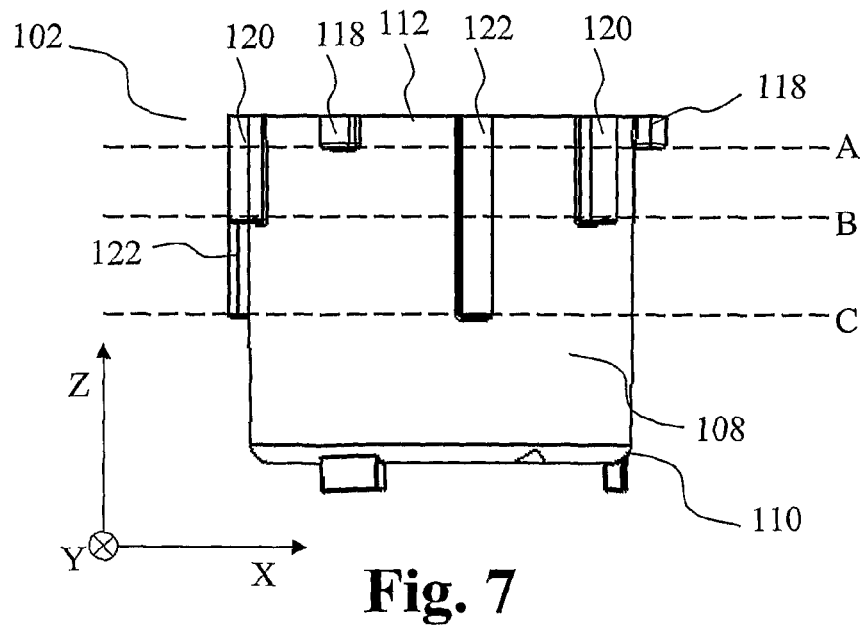

FIG. 7 is a side view of the culture insert in FIG. 6. A first set of protrusions 118 functions as suspension elements 117 on the outer surface 108 to suspend the culture insert in a first vertical position in a frame. In this embodiment, the first set of protrusions comprises three protrusions extending from positions in a first plane A indicated by a dotted line in the figure. Further, a second set of protrusions 120 functions as suspending elements on the outer surface 108 to suspend the culture insert in a second vertical position in a frame. In this embodiment, the second set of protrusions 120 comprises three protrusions extending from positions in a second plane B indicated by a dotted line in the figure. Furthermore, a third set of protrusions 122 functions as suspending elements on the outer surface 108 to suspend the culture insert in a third vertical position in a frame. In this embodiment, the third set of protrusions 122 comprises three protrusions extending from positions in a third plane C indicated by a dotted line in the figure.

The planes A, B and C are substantially parallel to the XY-plane. The membrane 114 extends in a plane parallel to the XY-plane, and the sidewall 104 extends in a direction along an axis parallel to the Z-axis.

The protrusions are flush with the second end of the sidewall, the second end extending in a plane parallel to the XY-plane. In another embodiment at least some of the protrusions extend from and to different vertical positions on the outer surface. For example, the third set of protrusions 122 may extend from positions on the outer surface in the plane C to positions on the outer surface in the plane A. Variations within a set of protrusions may occur. The vertical position of the planes A, B and C are indicated with dotted lines in the figure.

Figure 8:
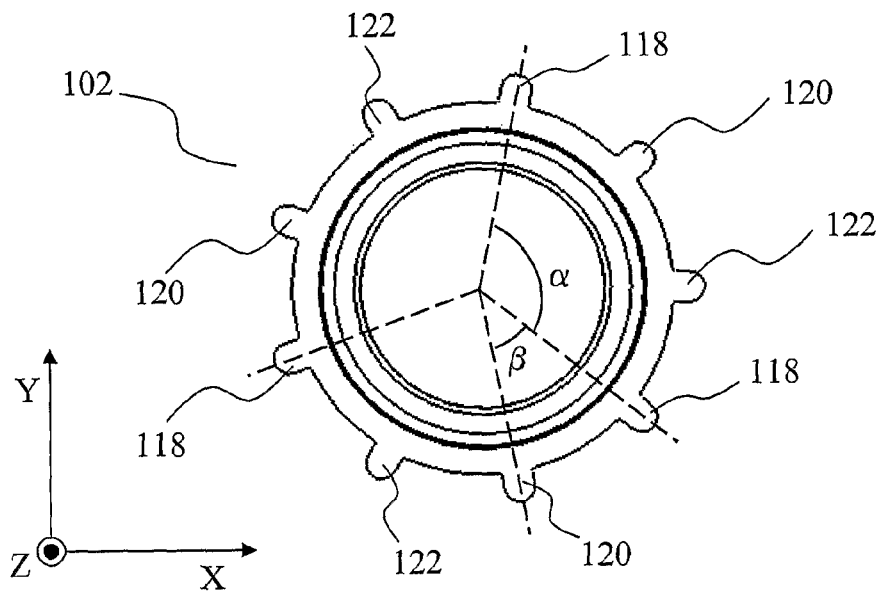

FIG. 8 shows the culture insert 102 seen from above. The protrusions within a set of protrusions, e.g. the first set of protrusions 118, are evenly distributed around the outer surface in a plane substantially parallel to XY-plane. Thus in this embodiment, where a set of protrusions consists of three protrusions, the protrusions within a set have a mutual angular distance of substantially 120° within the respective sets of protrusions 118, 120, 122. For example, the angle α indicates the mutual angular distance of 120° between two protrusions in the first set of protrusions 118.

The protrusions 118, 120, 122 for suspending the culture insert are substantially evenly distributed around the outer surface in a plane substantially parallel to XY-plane. In this embodiment, the mutual angular distance p between the nine protrusions 118, 120, 122 is about 40°.

Figure 9:
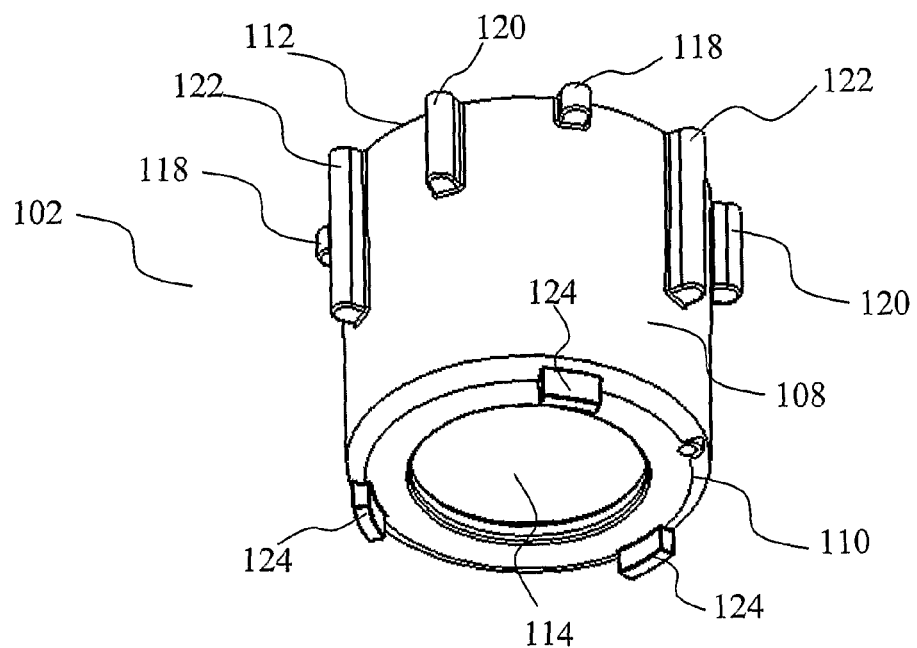

FIG. 9 shows the culture insert 102 in a perspective view from below. The culture insert has three supports 124 for maintaining a minimum distance between the membrane 114 and a surface, e.g. between the membrane and the bottom of a well of a culture tray.

Figure 10:
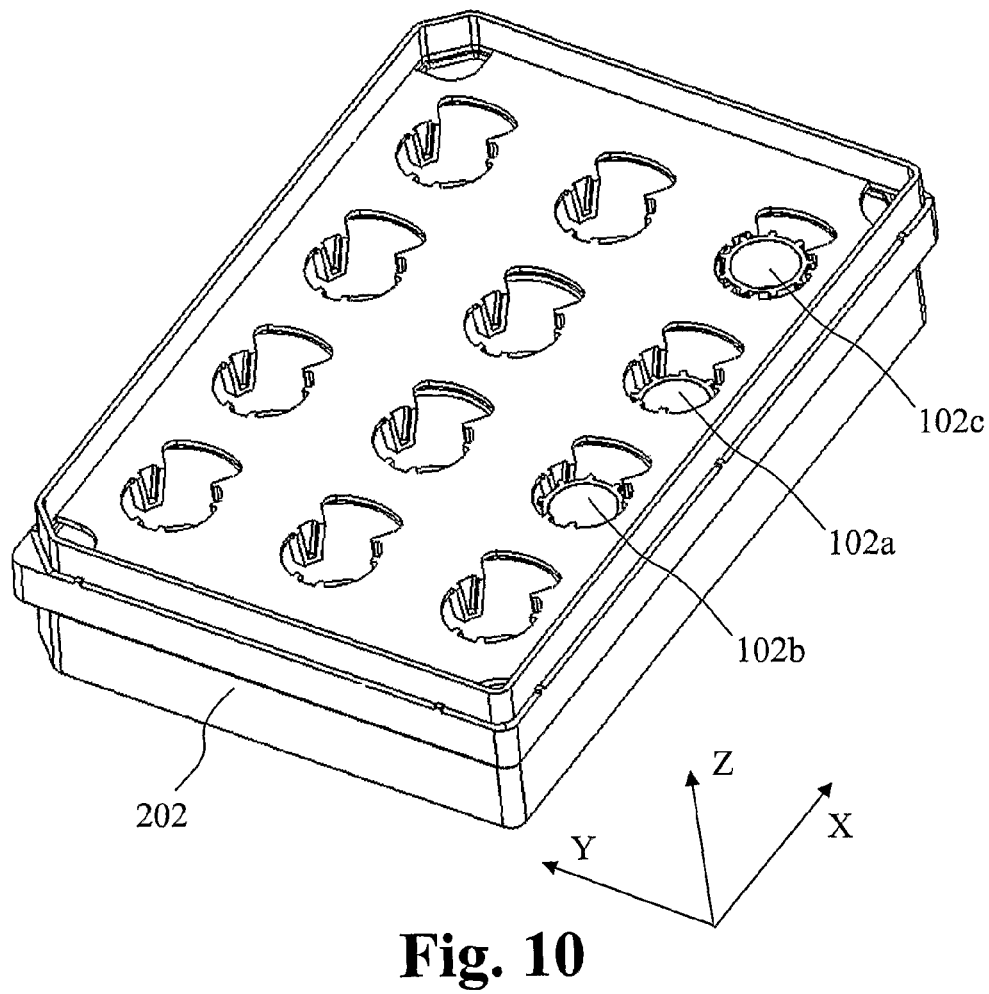
FIGS. 10-11 show a culture tray engaged with a culture insert carrier supporting three culture inserts in different vertical positions.

FIG. 10 shows a system comprising a culture insert carrier, at least one culture insert and a culture tray according to the invention. Three culture inserts 102a, 102b, 102c corresponding to the culture insert in FIGS. 6-9 are positioned in a first, second and third vertical position, respectively, in the culture insert carrier 2. The culture insert 102a is in a first vertical position suspended in the first set of protrusions 118, the protrusions being supported by the first rim 20, the second rim 26 and the third rim 32 in the culture insert carrier. The culture insert 102b is in a second vertical position suspended in the second set of protrusions 120, the protrusions being supported by the first rim 20, the second rim 26 and the third rim 32 in the culture insert carrier. The culture insert 102c is in a third vertical position suspended in the third set of protrusions 122, the protrusions being supported by the first rim 20, the second rim 26 and the third rim 32 in the culture insert carrier. The shape of the recesses in the support elements substantially prevents the culture inserts from rotating around an axis parallel to the Z-axis. Furthermore the lateral positions of the culture inserts are well defined providing easier manual and automatic handling of the culture inserts. An area of the openings in the culture insert carrier remains non-obstructed when a culture insert is inserted and supported in the culture insert carrier. Thus pipette access is provided to the one or more wells in the culture tray 202.

Figure 11:
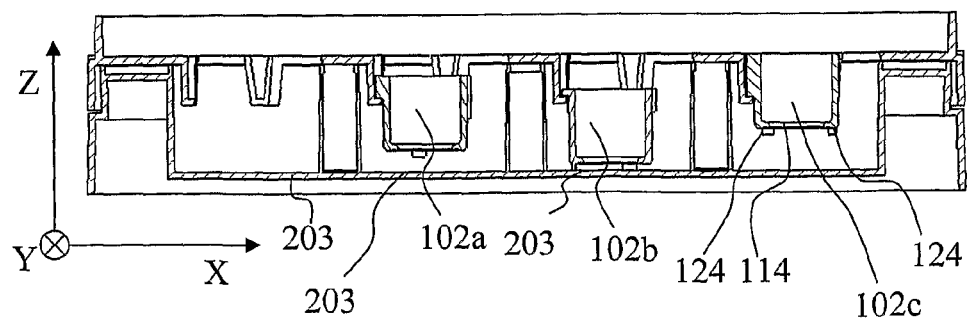

FIG. 11 shows a cross-section of the culture system in FIG. 10. The three culture inserts 102a, 102b, 102c are positioned in first, second and third vertical positions, respectively, such that the distances between the respective membranes and respective well bottoms 203 of the culture tray are different. The well bottom or bottoms extend in a plane parallel to the XY-plane.

Figure 12:
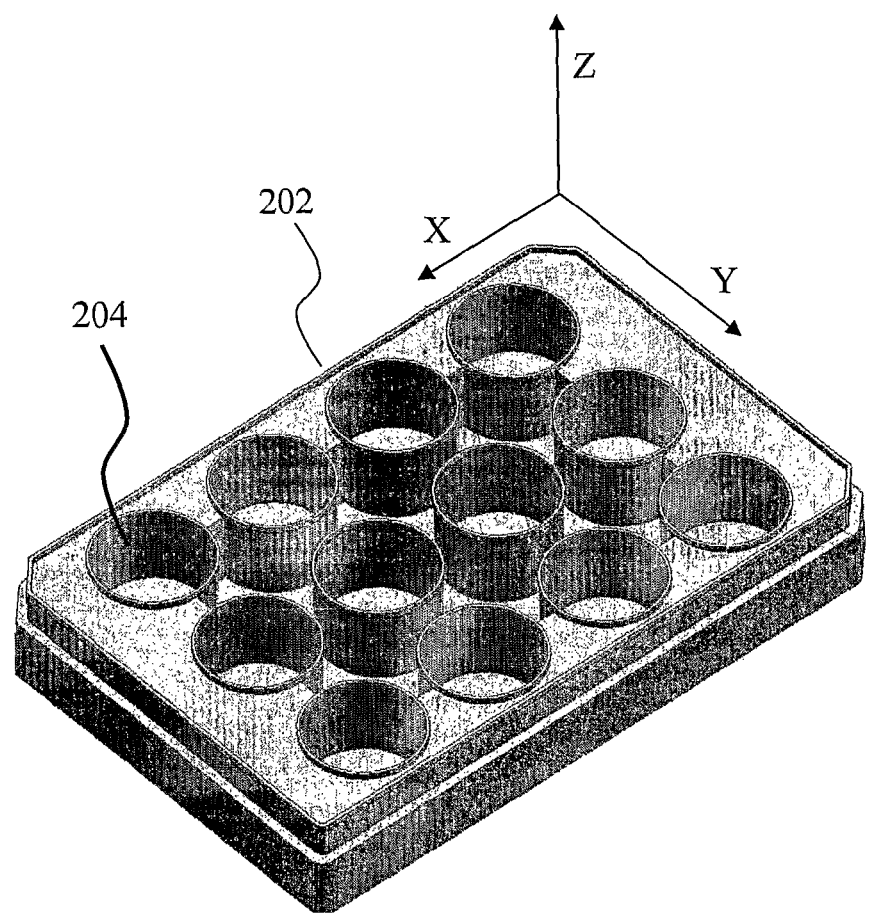
FIG. 12 shows a culture tray for use in a system according to the invention.

FIG. 12 shows a perspective view of a culture tray for a system according to the invention. The culture tray 202 comprises twelve wells 204.

Figure 13:
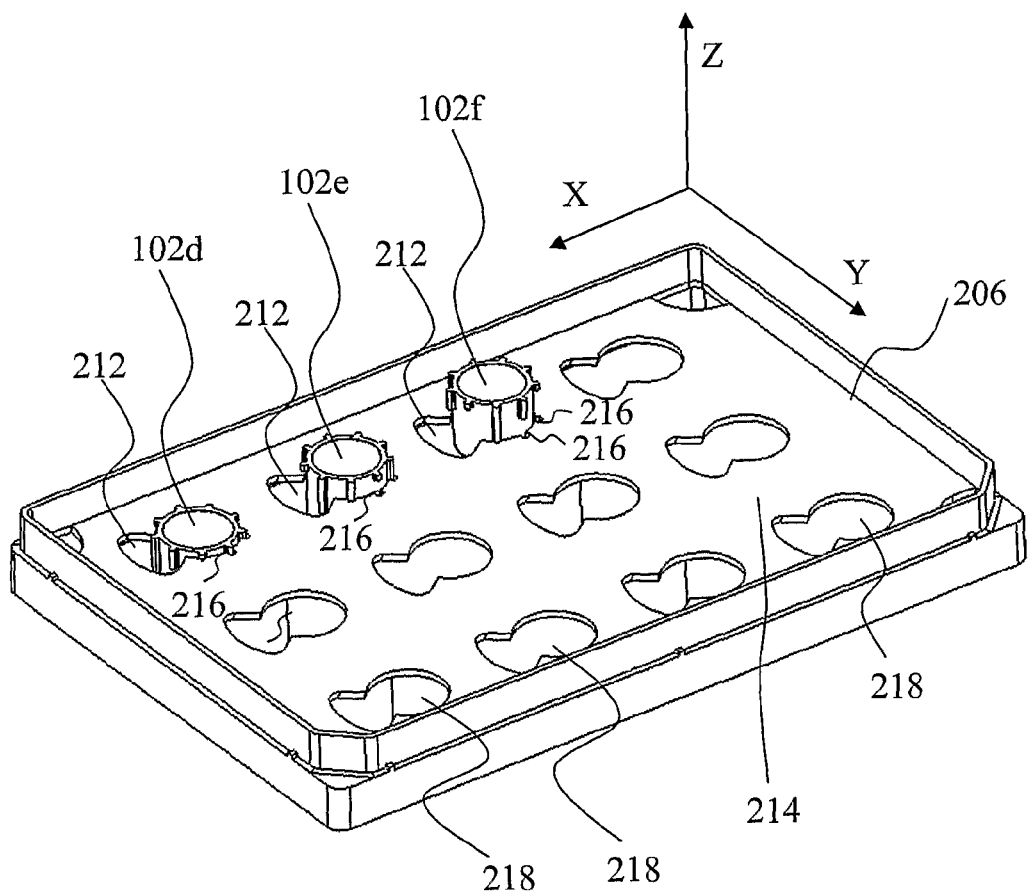
FIGS. 13-14 show views of another preferred embodiment of the culture insert carrier according to the invention accommodating culture inserts according to the invention.

FIG. 13 shows a perspective view of another embodiment of a culture insert carrier according to the invention. The culture insert carrier 206 accommodates three culture inserts 102d, 102e, 102f corresponding to the culture insert 102 in FIGS. 6-9 in three openings 212 of the plane member 214 that extends in the XY-plane. The culture inserts 102d is supported in a first vertical position by the first set of protrusions resting on the edge of the opening. The opening 212 has four notches 216 that are formed for reception and accommodation of the second and/or the third set of protrusions of the culture insert. In the first vertical position, protrusions of the second set and the third set of protrusions interact with the notches to prevent the culture insert from rotating. The culture insert 102e is supported in a second vertical position by the second set of protrusions resting on the edge of the opening. In the second vertical position, a protrusion or protrusions of the third set of protrusions interact with at least some of the notches, e.g. two, to prevent the culture insert from rotating. The culture insert 102f is supported in a third vertical position by the third set of protrusions resting on the edge of the opening. In this position, the culture insert can rotate substantially freely around an axis parallel to the Z-axis. The opening 218 is another embodiment of an opening that may support a culture insert in a position in a culture tray. Preferably, the one or more openings for culture inserts of a culture insert carrier according to the invention have the same shape and/or size, but as shown in FIG. 13, the one or more openings may vary in shape and/or size.

Figure 14:
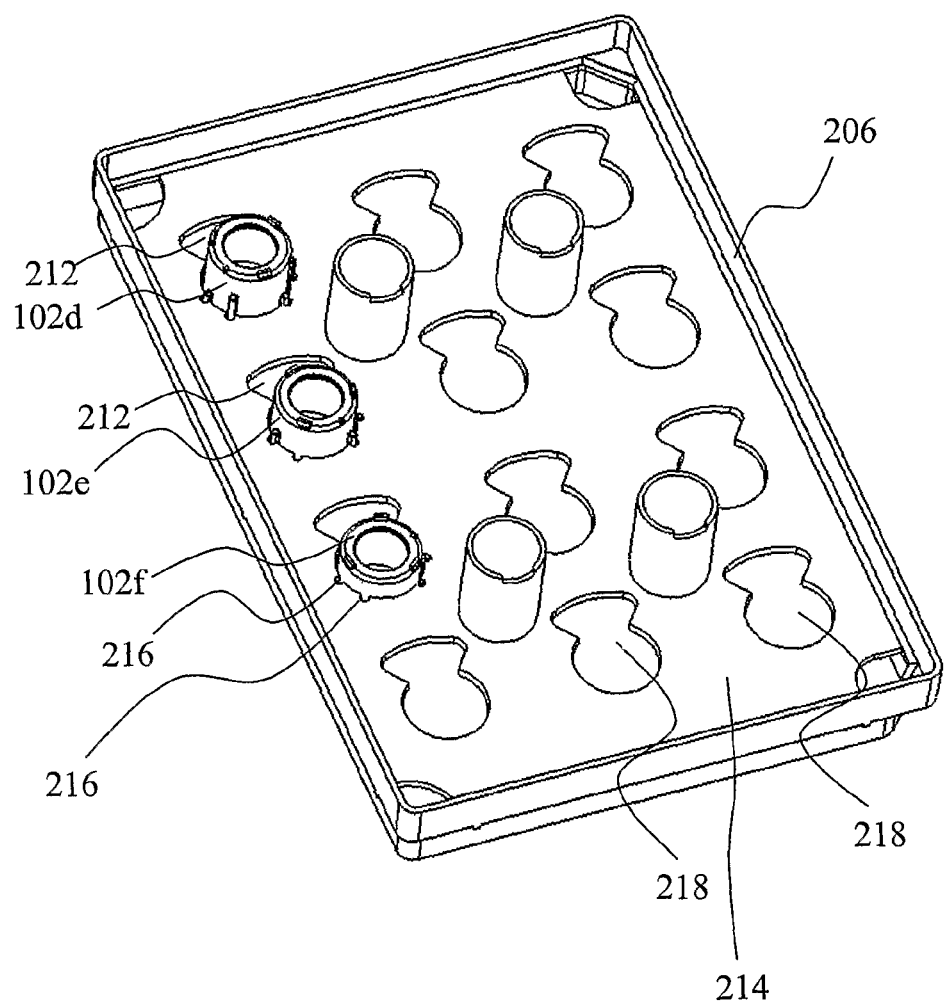

FIG. 14 shows the culture insert carrier 206 with culture inserts in a perspective view from below.

Figure 15:
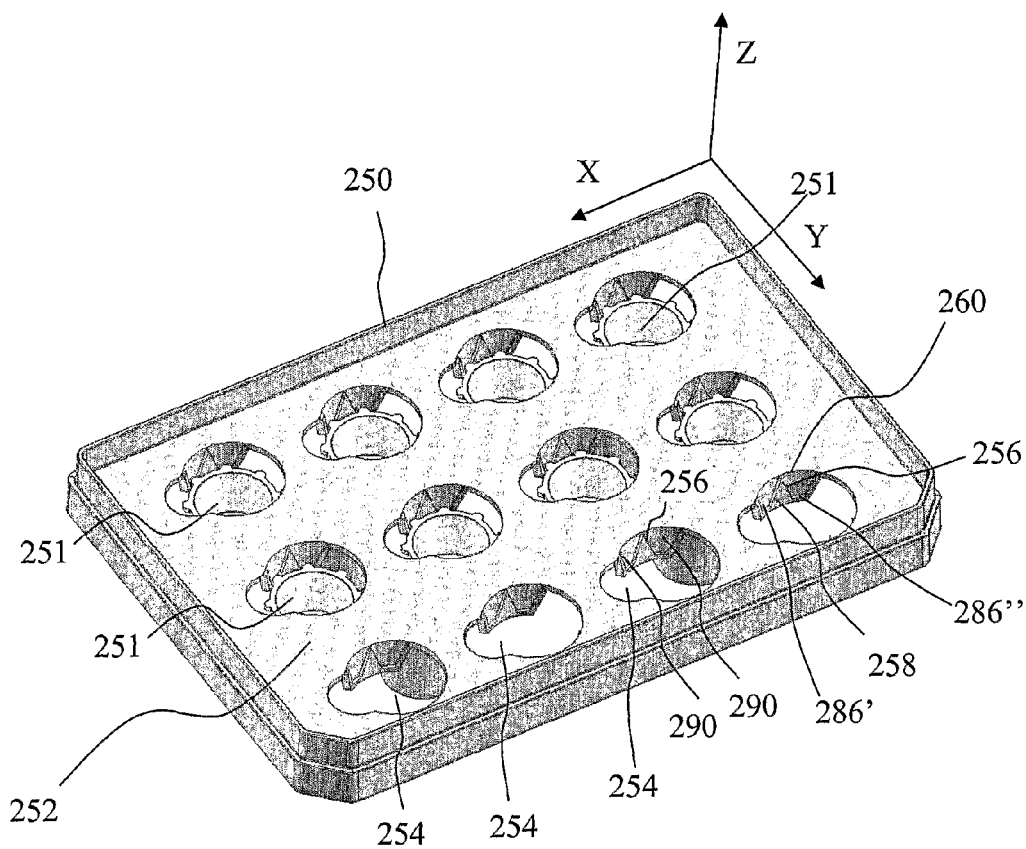
FIGS. 15-16 show views of another preferred embodiment of the culture insert carrier according to the invention accommodating culture inserts, FIG. 17 schematically shows an embodiment of a culture insert according to the invention and an opening of a culture insert carrier, and FIG. 18 schematically shows a culture system according to the invention.

FIG. 15 shows a perspective view of another embodiment of a culture insert carrier according to the invention. The culture insert carrier 250 accommodates eight culture inserts 251. The culture insert carrier 250 has a plane member 252 extending in the XY-plane and comprising twelve openings 254. An opening 254 has a first support element 256 with a bottom 258 and a top 260 and a second support element 280 with a bottom 282 and a top 284. The first support element 256 has a first set of rims 286, and the second support element 280 has a second set of rims 288. The first set of rims comprises two rims 286' and 286" and the second set of rims comprises two rims 288' and 288". The first support element 256 and the second support element 280 have substantially the same size and shape. In this embodiment the rims 286', 286", 288' and 288" extend in a plane substantially parallel to the plane member 252. A first set of recesses 290 forms the first set of rims 286 and a second set of recesses 292 forms the second set of rims 288. The rims 286', 288' may in another embodiment extend in a plane A substantially parallel to the plane member and the rims 286", 288" may extend in a plane B substantially parallel to the plane member, wherein the planes A and B are spaced apart. The first and second support elements may be joined to form a first support element having a first set of rims comprising four rims 286', 286", 288', 288". The culture inserts has a plurality of protrusions for supporting the culture insert in a position in the opening. Some or all of the protrusions rest on at least some of the rims 286', 286", 288', 288". The carrier inserts 251 have a well-defined lateral position in the culture insert carrier providing easier automatic and manual handling of the culture inserts. Further, the provision of a culture insert carrier according to the invention provides easier handling of a plurality of culture inserts. The insert carriers 251 are prevented from rotating around an axis parallel to the Z-axis due to the shape of the recesses in the respective support elements.

Figure 16:
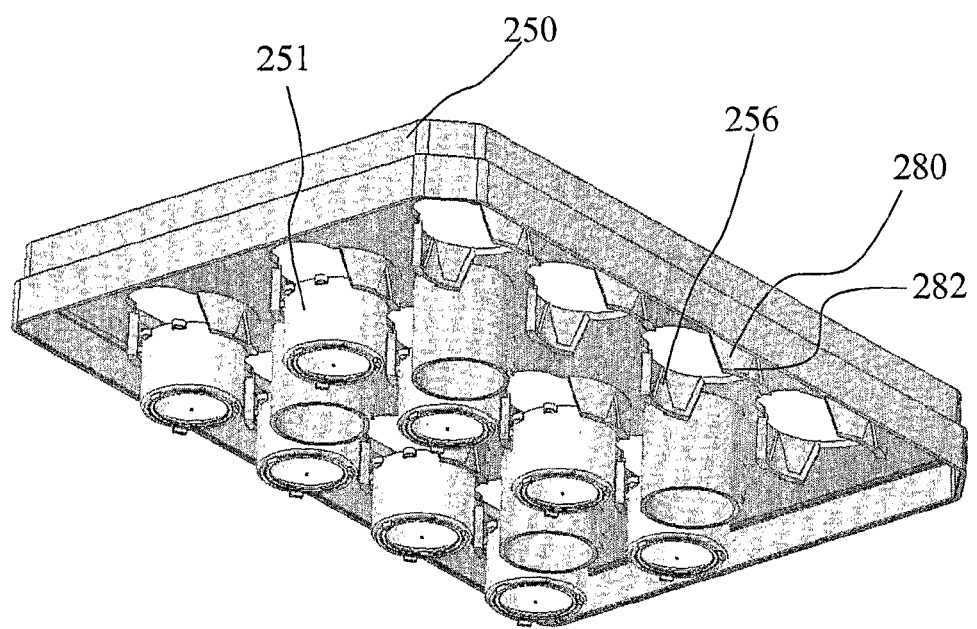

FIG. 16 shows the culture insert carrier 250 with culture inserts 251 in a perspective view from below.

Figure 17:
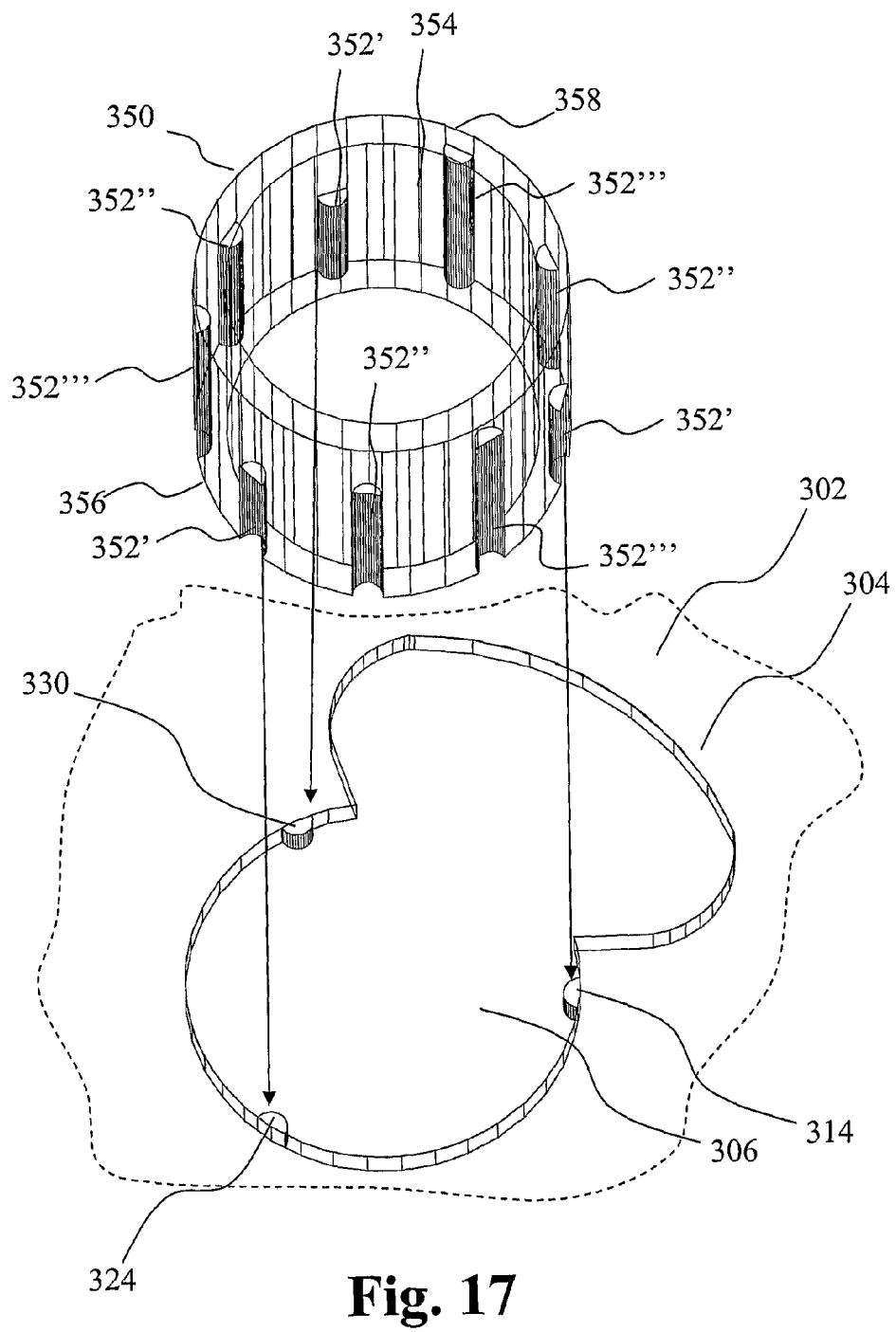

FIG. 17 schematically shows a part of a culture insert carrier 302 according to the invention having a plane member 304 with at least one opening 306. The opening 306 comprises a first support element 314 having a first protrusion forming a first rim, a second support element 324 having a second protrusion forming a second rim, and a third support element 330 having a third protrusion forming a third rim.

The support elements 314, 324, 330 are adapted to engage with corresponding suspension elements of a culture insert 350 according to the invention. The culture insert 350 comprises nine suspension elements 352 in the form of recesses. The suspension elements comprise a first set of recesses 352', a second set of recesses 352" and a third set of recesses 352''', each set of recesses being adapted to support the culture insert in a vertical position. The recesses 352', 352", 352''' are formed in the outer surface of the culture insert body 354 from the first end 356 towards the open second end 358.

Figure 18:
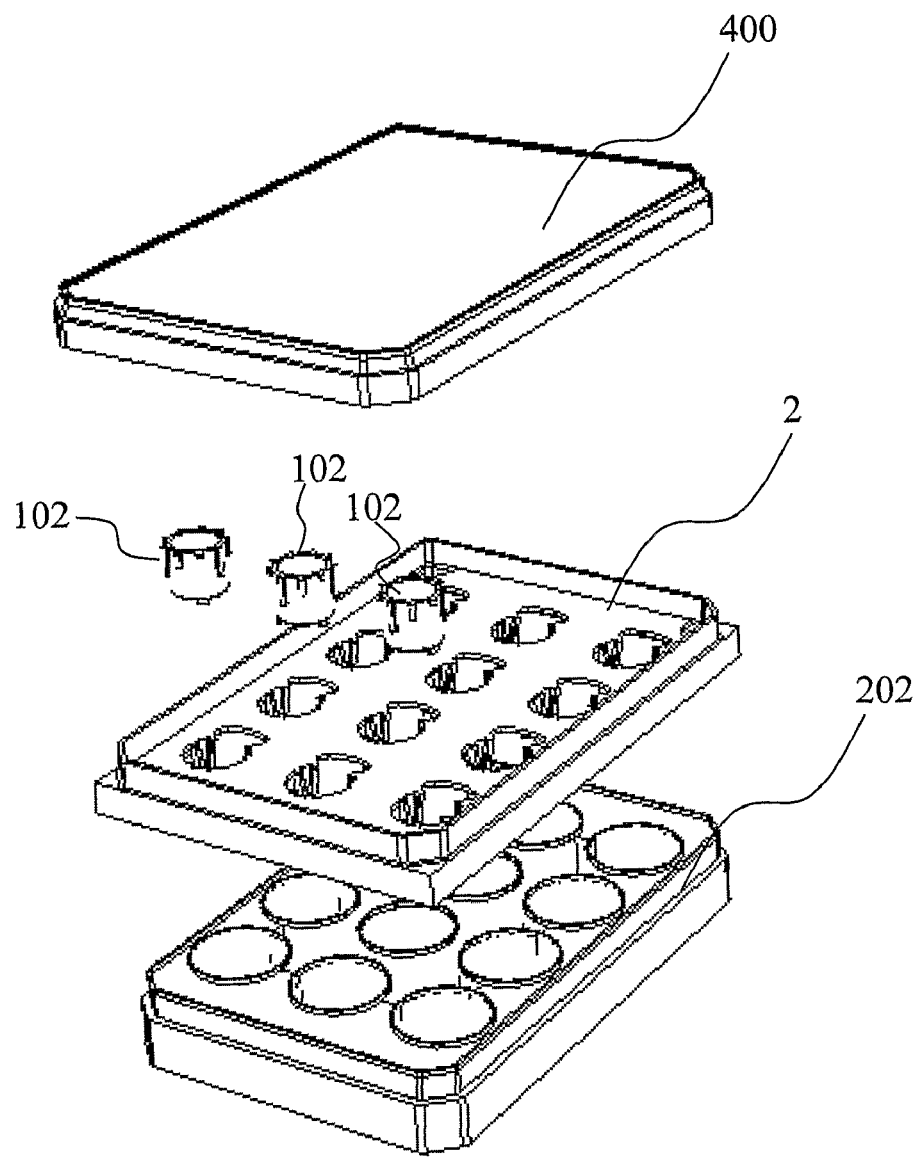

FIG. 18 shows an exploded view of a culture system according to the present invention. The system comprises a culture insert carrier 2, one or more culture inserts 102, a culture tray 202 and a lid 400. Preferably, the system comprises a culture insert for each opening in the culture insert carrier.

In specific embodiments, the invention relates to the following items:

1. A culture insert with a tubular sidewall comprising an inner surface and an outer surface and extending from a first end to a second end of the sidewall, a porous membrane positioned at the first end, a chamber delimited by the porous membrane and the sidewall and having an opening at the second end, and a plurality of suspension elements, wherein the suspension elements are adapted to suspend the culture insert in a plurality of vertical positions in relation to a frame.

2. A culture insert according to item 1, wherein the plurality of suspension elements comprises at least one set of protrusions for suspending the culture insert in at least two vertical positions.

3. A culture insert according to item 2, wherein the at least one set of protrusions comprises a first set of protrusions for suspending the culture insert in a first vertical position.

4. A culture insert according to any of items 2-3, wherein the at least one set of protrusions comprises a second set of protrusions for suspending the culture insert in a second vertical position.

5. A culture insert according to any of items 2-4, wherein the at least one set of protrusions comprises a third set of protrusions for suspending the culture insert in a third vertical position.

6. A culture insert according to any of items 2-5, wherein the protrusions within a set are evenly distributed along the outer surface in a plane substantially parallel to the membrane.

7. A culture insert according to any of items 2-6, wherein each of the sets of protrusions consists of three protrusions positioned at a mutual angular distance of about 120° along the outer surface in a plane substantially parallel to the membrane.

8. A culture insert according to any of items 2-7, wherein the plurality of protrusions are substantially evenly distributed along the outer surface in a plane substantially parallel to the membrane.

The culture insert according to the invention may be employed in a culture system comprising a culture insert carrier according to the invention.

The invention claimed is:

1. A culture system comprising:
   at least one culture insert comprising a culture insert body having first and second ends with a membrane positioned at the first end, and at least first and second suspension elements;
   a culture insert carrier for supporting the at least one culture insert in at least a first vertical position and a second vertical position, the culture insert carrier comprising a plane member with at least one opening having at least one support element, the at least one opening in the culture insert carrier being shaped to support the at least one culture insert for insertion and removal of the at least one culture insert in the culture insert carrier;
   wherein the first suspension element comprises a set of first surfaces located at a first distance from the first end of the culture insert body and the second suspension element comprises a second set of surfaces located at a second distance from the first end of the culture insert body, said second distance different from the first distance;
   wherein the set of first surfaces rests on the at least one support element in the first vertical position; and
   wherein the set of second surfaces rests on the at least one support element in the second vertical position.

2. A culture system according to claim 1, wherein the at least one culture insert comprises at least two support elements.

3. A culture system according to claim 1, wherein the culture system further comprises a culture tray having at least one well.

4. A culture system according to claim 1, wherein the at least one opening has an area that remains unobstructed for pipette access after insertion of the culture insert.

5. A culture system according to claim 3, wherein the plane member comprises at least one pipette opening for pipette access to the at least one well of the culture tray.

* * * * *